(12) United States Patent
Shay

(10) Patent No.: US 9,572,931 B2
(45) Date of Patent: Feb. 21, 2017

(54) DEVICE, SYSTEM AND METHOD FOR SELF-ADMINISTRATION OF A TREATMENT FLUID

(71) Applicant: AMBU A/S, Ballerup (DK)

(72) Inventor: Ofer Shay, Kfar Vradim (IL)

(73) Assignee: AMBU A/S, Ballerup (DK)

( * ) Notice: Subject to any disclaimer, the term of this patent is extended or adjusted under 35 U.S.C. 154(b) by 767 days.

(21) Appl. No.: 13/927,131

(22) Filed: Jun. 26, 2013

(65) Prior Publication Data

US 2013/0345659 A1  Dec. 26, 2013

Related U.S. Application Data

(60) Provisional application No. 61/664,161, filed on Jun. 26, 2012.

(51) Int. Cl.
*A61M 5/168* (2006.01)
*A61M 5/142* (2006.01)

(52) U.S. Cl.
CPC ....... *A61M 5/16804* (2013.01); *A61M 5/1424* (2013.01); *A61M 5/14212* (2013.01); *A61M 5/14216* (2013.01); *A61M 5/16813* (2013.01)

(58) Field of Classification Search
CPC .................... A61M 5/16804; A61M 5/16813; A61M 5/14212; A61M 5/14216; A61M 5/1424

See application file for complete search history.

(56) References Cited

U.S. PATENT DOCUMENTS

| | | | | |
|---|---|---|---|---|
| 3,782,380 | A | * | 1/1974 | Van Der Gaast ....... A61M 5/30 222/340 |
| 4,828,551 | A | * | 5/1989 | Gertler ................ A61M 5/1424 604/208 |
| 5,306,257 | A | | 4/1994 | Zdeb |
| 5,360,411 | A | | 11/1994 | Sciacca |
| 5,514,096 | A | | 5/1996 | Hiejima et al. |
| 5,531,688 | A | | 7/1996 | Hiejima et al. |
| 5,776,105 | A | | 7/1998 | Corn |
| 6,056,727 | A | | 5/2000 | O'Neil |
| 6,231,560 | B1 | | 5/2001 | Bui et al. |
| 6,719,728 | B2 | * | 4/2004 | Mason ................ A61M 5/1424 604/131 |
| 6,802,823 | B2 | | 10/2004 | Mason |
| 6,899,695 | B2 | | 5/2005 | Herrera |
| 7,083,593 | B2 | | 8/2006 | Stultz |

(Continued)

*Primary Examiner* — Laura Bouchelle
(74) *Attorney, Agent, or Firm* — Faegre Baker Daniels LLP

(57) ABSTRACT

A device, system and method for self-administration of a bolus dosage of a treatment fluid are disclosed. A device according to embodiments of the present invention may comprise a housing comprising an external lever operable by a user, an internal lever, for applying pressure to a compression spring, which in turn may press a piston to pressurize treatment fluid contained in an internal reservoir, in a high flow rate, through a small diameter catheter, into a patient body. A system according to some embodiment may comprise a device having an external reservoir connected to an inlet thereof, and a catheter connected to an outlet thereof. A method according to some embodiments may comprise actuating levers of the device, compressing a partially loaded compression spring contained in a spring cage, and pressurizing fluid contained in an internal reservoir of the device to be released through an outlet of the device.

22 Claims, 24 Drawing Sheets

(56) References Cited

U.S. PATENT DOCUMENTS

| | | |
|---|---|---|
| 7,192,414 B2 | 3/2007 | Stultz |
| 7,204,823 B2 | 4/2007 | Estes et al. |
| 7,309,333 B2 | 12/2007 | Mason |
| 7,419,322 B2 | 9/2008 | LaFlamme et al. |
| 7,431,717 B2 | 10/2008 | Gonzales |
| 7,517,335 B2 | 4/2009 | Gravesen et al. |
| 7,651,489 B2 | 1/2010 | Estes et al. |
| 7,837,647 B2 | 11/2010 | Hahn et al. |
| 7,905,865 B2 | 3/2011 | Lee |
| 7,914,483 B2 | 3/2011 | Simmons |
| 7,997,454 B2 | 8/2011 | LaFlamme et al. |
| 8,012,119 B2 | 9/2011 | Estes et al. |
| 8,061,566 B2 | 11/2011 | LaFlamme et al. |
| 8,100,890 B2 | 1/2012 | Kriesel et al. |
| 8,113,244 B2 | 2/2012 | Kamen et al. |
| 8,123,073 B2 | 2/2012 | LaFlamme et al. |
| 8,132,696 B2 | 3/2012 | Mileti |
| 8,147,451 B2 | 4/2012 | Brockman et al. |
| 8,230,744 B2 | 7/2012 | Gravesen et al. |
| 8,271,106 B2 | 9/2012 | Wehba et al. |
| 8,292,876 B2 | 10/2012 | Kriesel et al. |
| 8,303,574 B2 | 11/2012 | Gray et al. |
| 8,308,688 B2 | 11/2012 | Valle et al. |
| 8,323,246 B2 | 12/2012 | Chiravuri et al. |
| 8,361,010 B2 | 1/2013 | Simmons |
| 8,387,833 B2 | 3/2013 | LaFlamme et al. |
| 8,414,522 B2 | 4/2013 | Kamen et al. |
| 8,435,214 B2 | 5/2013 | Gray et al. |
| 8,496,646 B2 | 7/2013 | Kamen et al. |
| 8,500,702 B2 | 8/2013 | Estes et al. |
| 8,518,000 B2 | 8/2013 | Gray et al. |
| 8,545,445 B2 | 10/2013 | Kamen et al. |
| 8,579,884 B2 | 11/2013 | Lanier, Jr. et al. |
| 8,585,377 B2 | 11/2013 | Kamen et al. |
| 8,622,991 B2 | 1/2014 | Pesach et al. |
| 2008/0097317 A1 | 4/2008 | Alholm et al. |
| 2008/0281297 A1 | 11/2008 | Pesach et al. |
| 2009/0054867 A1 | 2/2009 | Gravesen et al. |
| 2010/0174225 A1 | 7/2010 | Pesach et al. |
| 2010/0249718 A1 | 9/2010 | Ishizaki et al. |
| 2012/0035547 A1 | 2/2012 | Estes et al. |
| 2012/0041414 A1 | 2/2012 | Estes et al. |
| 2012/0053556 A1 | 3/2012 | Lee |
| 2012/0310152 A1 | 12/2012 | Wehba et al. |
| 2013/0053775 A1 | 2/2013 | Chiravuri et al. |
| 2013/0116630 A1 | 5/2013 | Valle et al. |
| 2013/0123745 A1 | 5/2013 | Simmons |

* cited by examiner

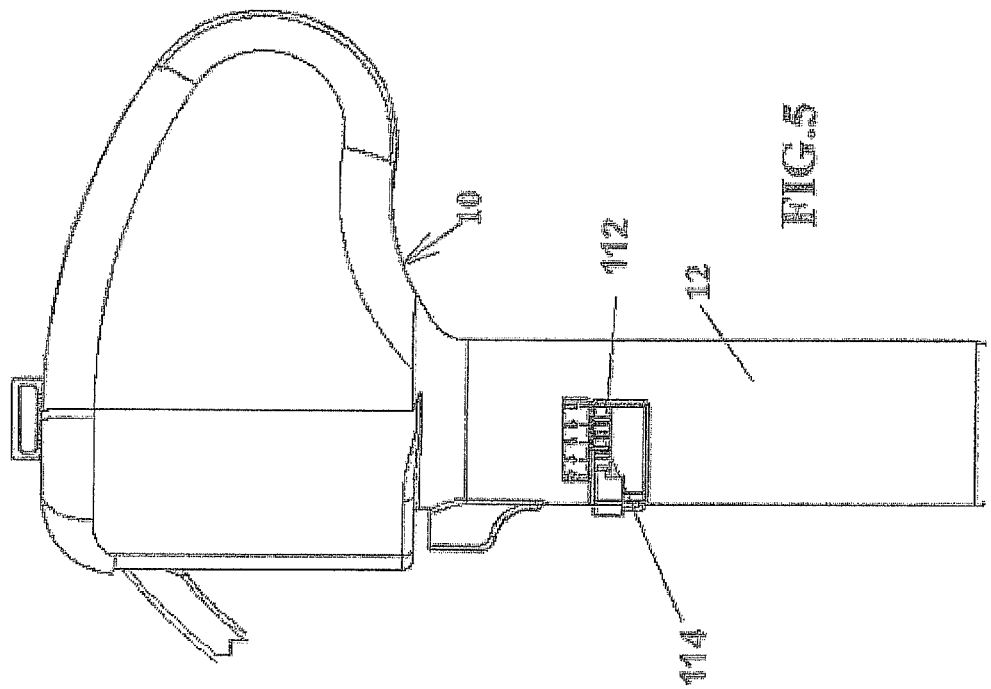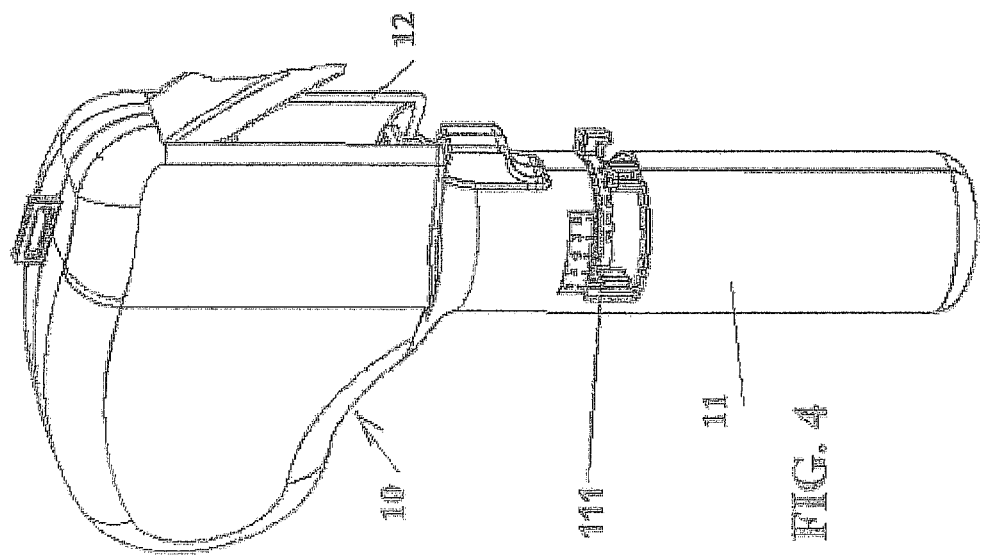

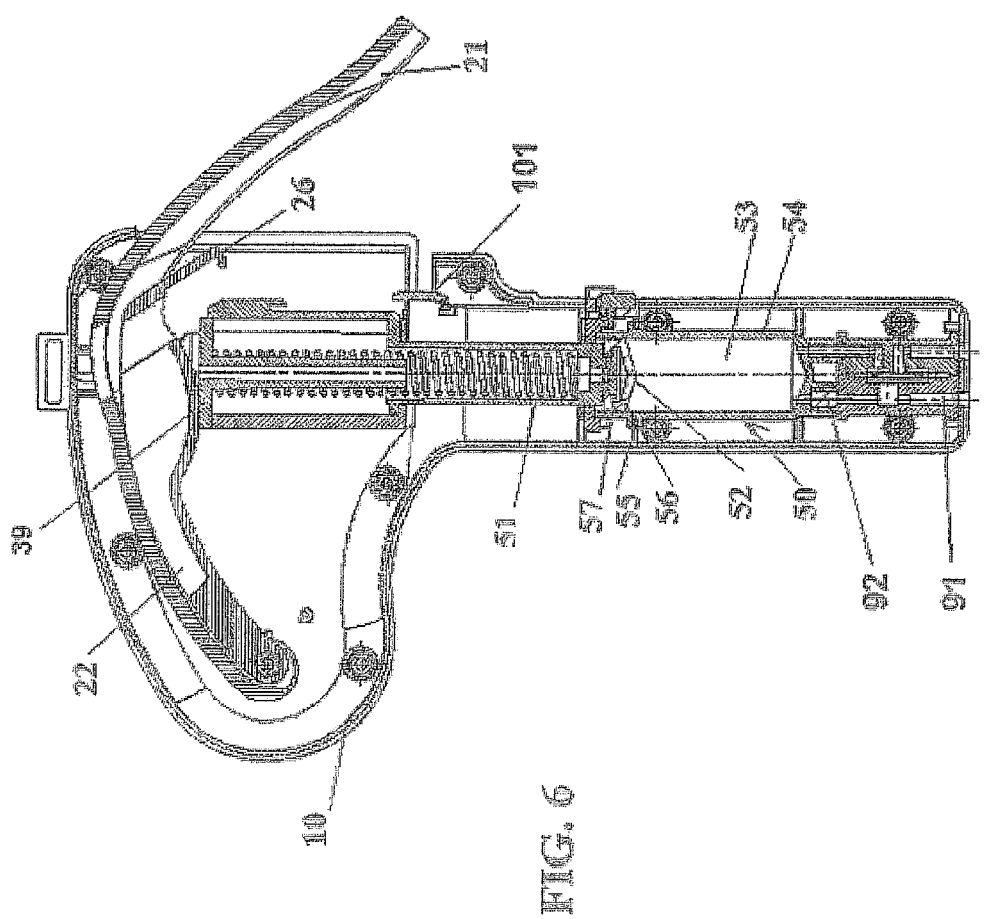

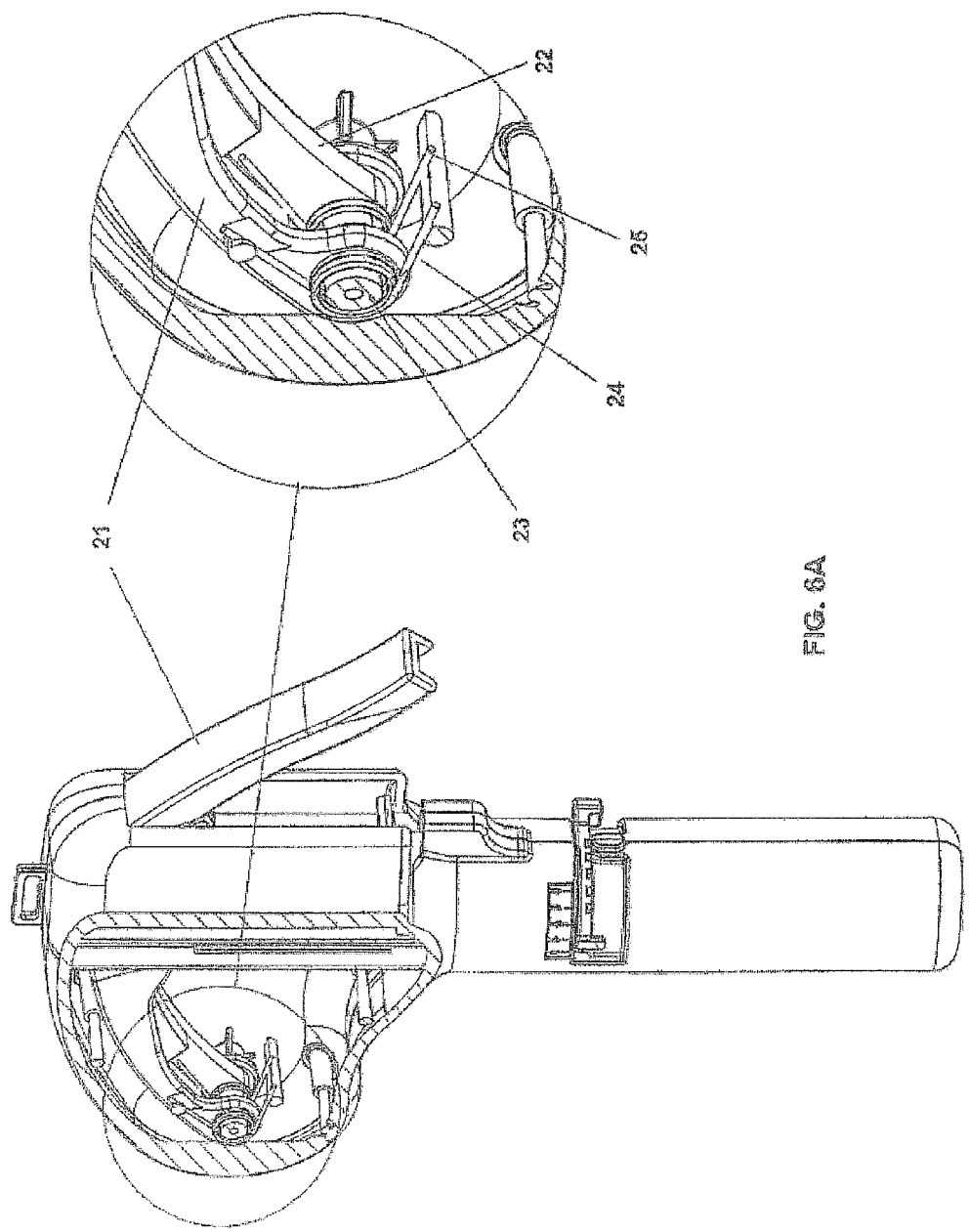

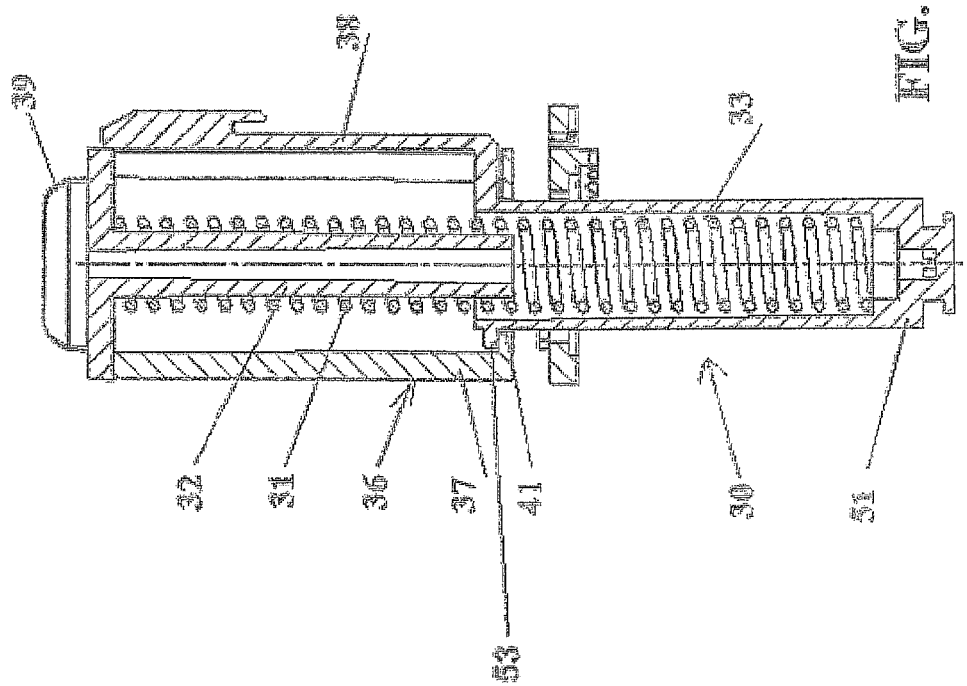

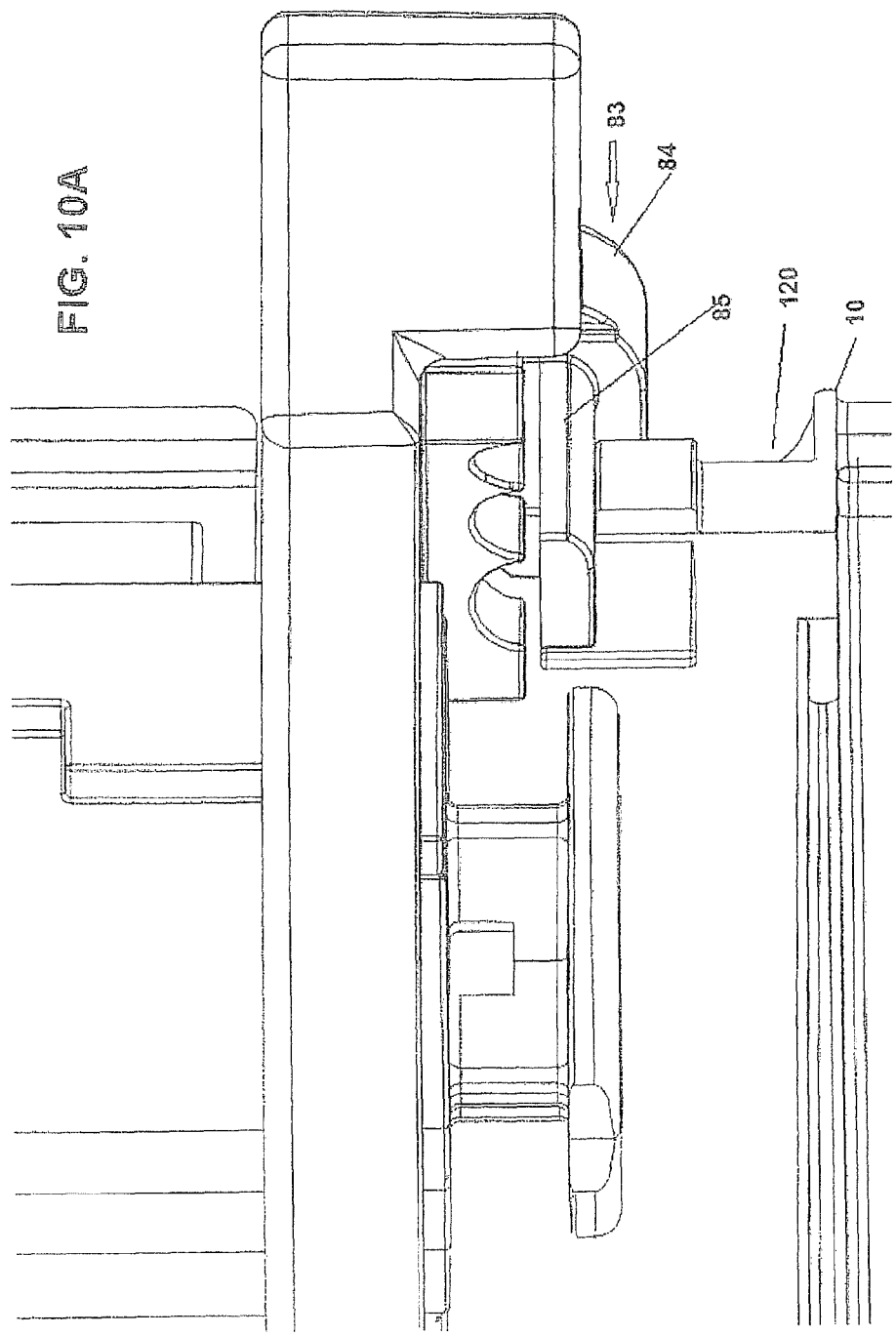

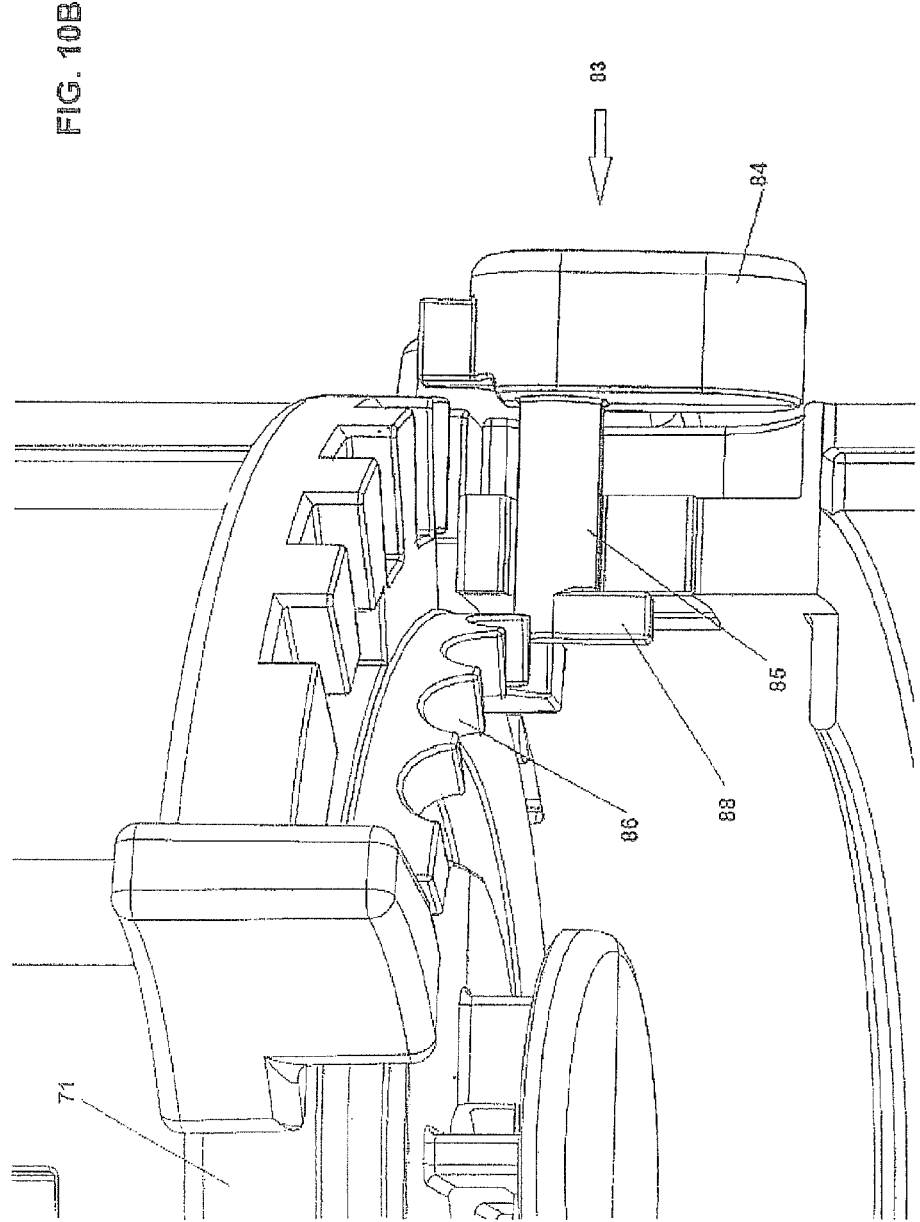

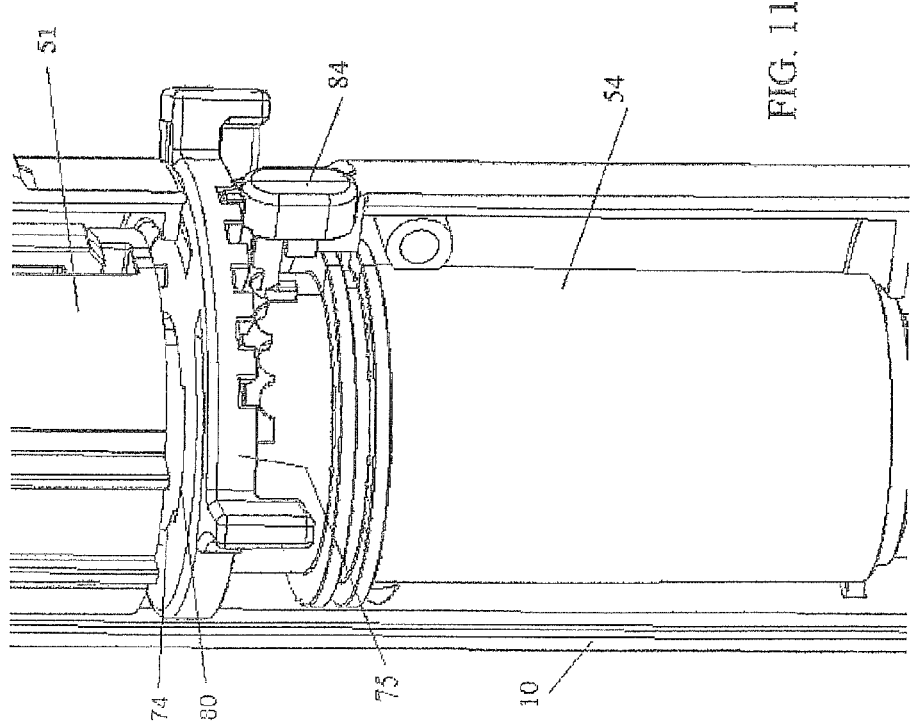

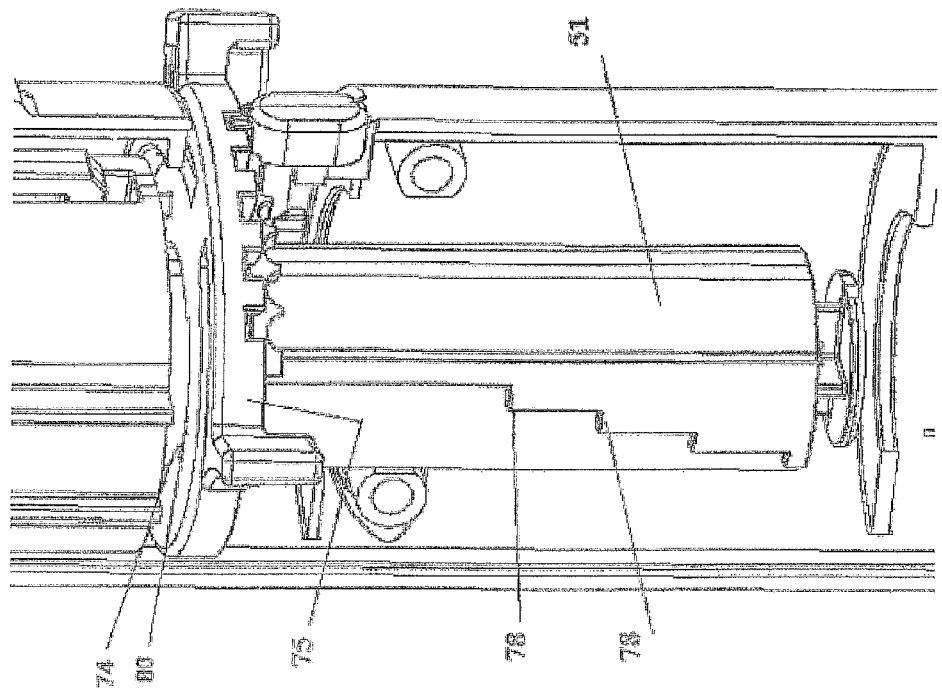

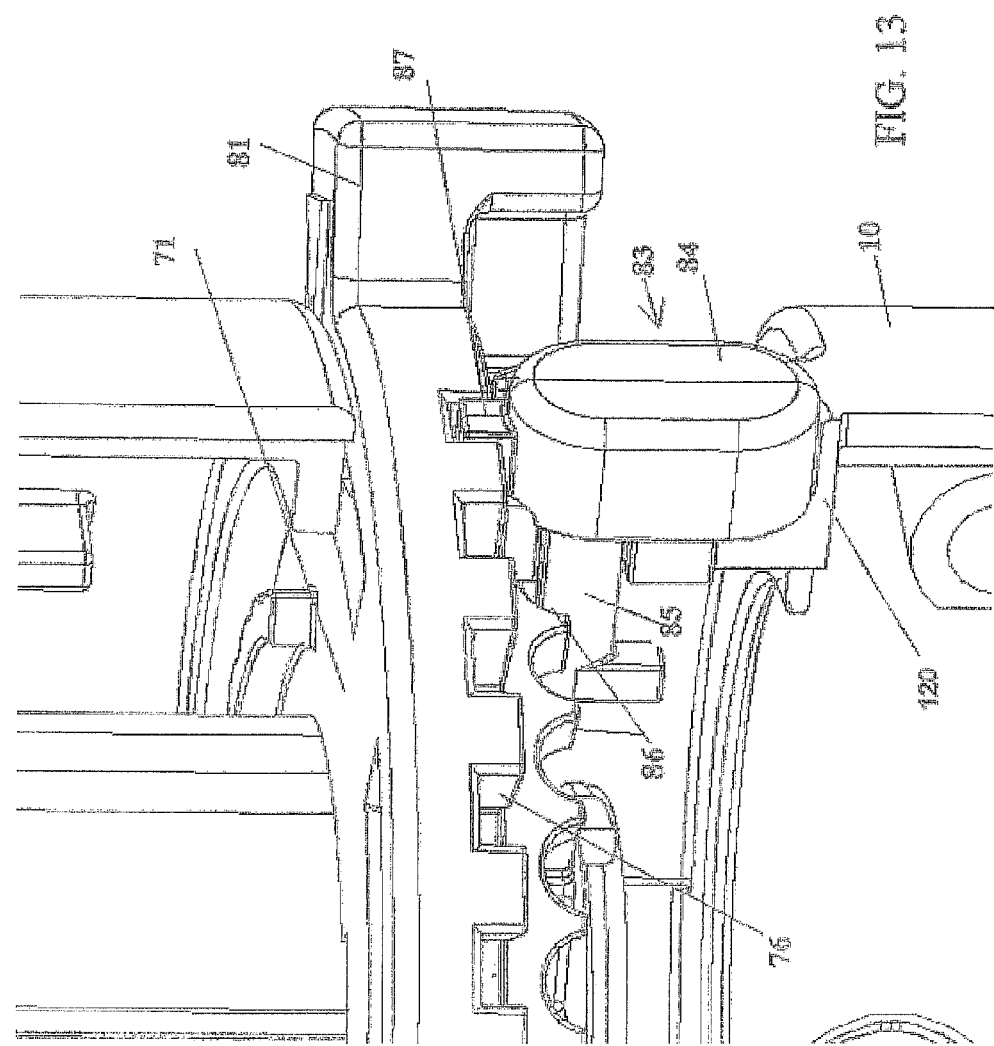

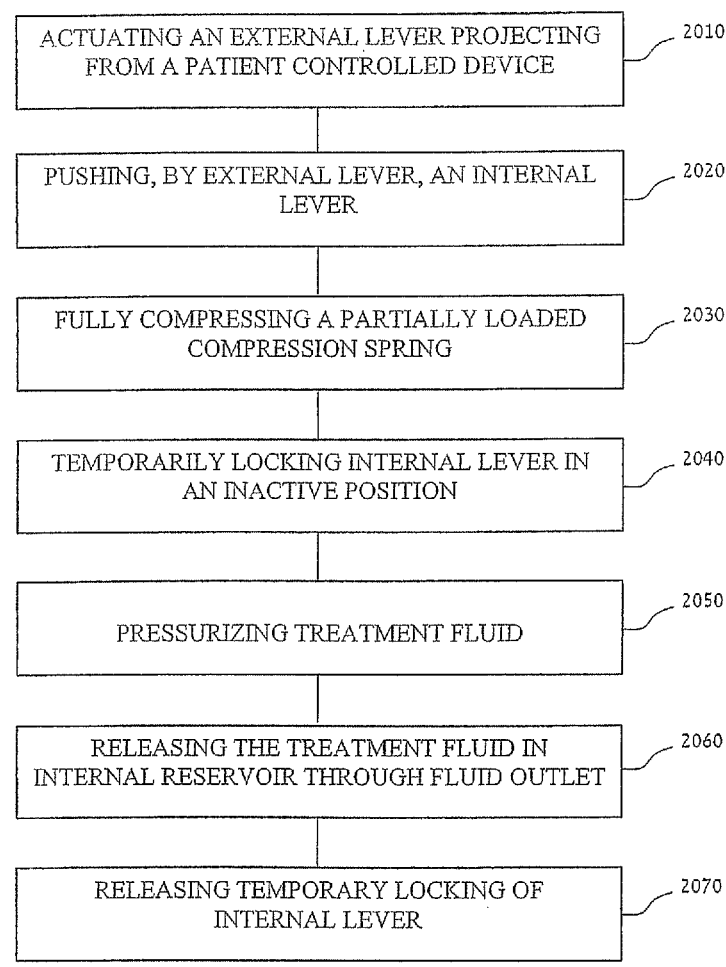

DEVICE, SYSTEM AND METHOD FOR SELF-ADMINISTRATION OF A TREATMENT FLUID

CROSS REFERENCE TO RELATED APPLICATIONS

This application claims the benefit of U.S. Provisional Patent Application No. 61/664,161, filed on Jun. 26, 2012, which is incorporated herein by reference in its entirety.

BACKGROUND OF THE INVENTION

Since the early 1990's, the use of infusion pumps to continuously administer anesthetic medications has been common practice for achieving long term continuous regional anesthesia (such pumps are sometimes referred to as "pain-pumps"). These pumps are either electro-mechanical pumps or mechanical pumps, most of them designed to be ambulatory, utilizing a carrying pouch or similar means.

Post-operative patients and some oncology patients are among those who may require continuous regional anesthesia, which can be achieved by the steady infusion of an analgesic medication, supplied subcutaneously and/or submuscularly by means of an infusion pump connected to a designated catheter. The designated catheter is connected to the patient, who normally receives a dosage of about 2 ml/hr to 12 ml/hr therethrough.

Postoperative patients may suffer severe pain, for example, as a result of movements or of unpredictable incidence. Such severe pain is addressed either by complementary medications or by adding additional anesthetic medication doses.

Currently, there are two main clinical procedures that are used for continuous long terms regional anesthesia. The first method is Surgical Site Infiltration (SSI, or sometimes called Wound Bathing), in which the medication is introduced into or near to the surgical incision by the use of a catheter with a long fenestrated segment inserted into the patient body tissue. The second method is Continuous Peripheral Nerve Block (CPNB), in which the medication is introduced close to the main nerve that controls the area of the pain source (mainly, the area of the surgical incision).

Some pumps are equipped with a Patient Control Analgesia (PCA) device that enables the patient to administer additional medication to deal with severe pain. When the PCA device is activated, a relatively large medication volume (bolus) is injected at a relatively high flow-rate. In parallel PCA administration (the most common version), the bolus medication is in addition to the pump basal flow. In in-line (series) administration, only the bolus medication is delivered. Efficient pain blockage is achieved once the nerve cord is fully circulated with the anesthetic medication. Fully circulated medication spread over the nerve cord is achieved with bolus' flow rate of at-least 5 ml/minute to 6 ml/minute, while the volume of medication delivered is typically between 4 ml to 10 ml, depending on the specific nerve that is being blocked.

As a result of the high hydraulic resistance of a typical Nerve Blocking (NB) catheter, the maximum bolus flow rate of the prior art infusion pumps is about 1.0 ml/minute to 1.5 ml/minute.

Furthermore, prior art mechanical devices fail to efficiently and safely prevent parallel continuous flow through the bolus unit when not being activated. Moreover, the designs of prior art mechanical devices fail to be intuitively activated by those out-patients who have been trained only shortly after being released from the recovery room and don't recall how to activate the bolus unit.

SUMMARY OF THE INVENTION

Embodiments of the present invention provide a patient controlled device, for self-administration of medication. Some embodiments of the present invention may comprise a housing comprising: a first lever projecting from the housing; a second lever, internal to the housing; the first lever and the second lever may pivoted by a mutual pin; the second lever may be adapted to apply force to press a partially preloaded compression spring contained within a spring cage; an internal reservoir; a plunger; a fluid inlet; a fluid outlet; and a capillary tube connected to said fluid inlet, said capillary tube may be adapted to control the flow rate into the internal reservoir.

According to some embodiments, the second lever may be adapted to apply compressive force to press the spring cage; and the spring cage compresses the compression spring when compressive force is applied thereto. As a result, the compression spring may apply force over said plunger when compressed by said spring cage, to release an accurate preset medication bolus dosage from the internal reservoir through the fluid outlet.

According to some embodiments of the present invention, the device may further comprise a dose adjustment mechanism adapted to set the volume of fluid allowed into the internal reservoir.

According to yet another embodiment, the device may further comprise a lock tooth adapted to temporarily retain the second lever in an inactive position until said internal reservoir is empty.

The self-administration device according to some embodiments may further comprise a diaphragm adapted to prevent flow through the fluid outlet when the internal lever is in an active position and to prevent back flow from said internal reservoir through said fluid inlet when fluid is released from said internal reservoir.

According to some embodiments, the plunger may further comprise a release tooth, the release tooth may be adapted to release the lock tooth when the internal reservoir is empty and thus to allow the internal lever to return to an active position.

The device according to some embodiments may further comprise a lever spring to return the internal lever to an active position when the lock tooth is released.

Embodiments of the present invention further provide a patient controlled system for self-administration of a treatment fluid. The system may comprise: an external infusion reservoir; a patient controlled device, for self-administration of treatment fluid to the patient body, the patient controlled device may comprise a housing comprising: a partially loaded compression spring contained within a spring cage; an internal reservoir; a plunger; a fluid inlet; a fluid outlet; and a capillary tube connected to the fluid inlet, the capillary tube may be adapted to control the flow rate into the internal reservoir; an hydraulic valve, positioned at the device fluid outlet, for preventing flow when the patient controlled device is inactive; and a catheter connected to the fluid outlet of said patient controlled device. According to some embodiments, the compression spring is adapted to apply force over the plunger when compressed by the spring cage, to release an accurate preset medication bolus dosage from the internal reservoir through the fluid outlet to the catheter.

According to some embodiments, the system may further comprise a dose adjustment mechanism adapted to set the volume of fluid allowed into the internal reservoir.

The system, according to some embodiments, may further comprise a lock tooth adapted to temporarily retain the second lever in an inactive position until the internal reservoir is empty.

According to some embodiments of the present invention, the system may further comprise a diaphragm adapted to prevent flow through said fluid outlet when pressurized fluid flows into said internal reservoir and to prevent back flow from said internal reservoir through said fluid inlet when fluid is released from said internal reservoir.

According to other or additional embodiments, the plunger may further comprise a release tooth, the release tooth adapted to release the lock tooth when the internal reservoir is empty.

According to some embodiments, the system may further comprise a lever spring to return said internal lever to an active position when said lock tooth is released.

According to some embodiments, the patient controlled device is connected to the external reservoir and to the catheter in parallel to allow continues flow of treatment fluid from the external reservoir to the patient body. According to other embodiments, the patient controlled device is connected to said external reservoir and to said catheter in series to prevent continues flow of treatment fluid from said external reservoir to said patient body.

According to some embodiments, the external reservoir is an elastomeric reservoir.

Embodiments of the present invention further provide a method for self-administration of a bolus dosage of treatment fluid by a patient, the method may comprise: actuating an external lever projecting from a patient controlled device for self-administration of treatment fluids to a patient body; pushing, by said external lever, an internal lever mutually pivoted therewith; fully compressing a partially loaded compression spring; temporarily locking said internal lever in an inactive position when said compression spring is fully compressed; pressurizing treatment fluid, contained within an internal reservoir, by said compression spring; releasing substantially all the volume of said treatment fluid in said internal reservoir through an outlet of said patient controlled device to a catheter; and releasing said temporary locking of said internal lever from said inactive position to an active position when said internal reservoir is empty.

According to some embodiments, the method may further comprise refilling the internal reservoir with treatment fluid from an external infusion pump.

According to some embodiments, the method may further comprise presetting a maximum bolus dosage releasable in each activation of the patient controlled device.

According to some embodiments, the preset dosage is lockable, to prevent administration of doses different from the preset dosage.

According to another embodiment of the present invention, the method may further comprise automatically refilling the internal reservoir with treatment fluid from an external infusion pump, up to the preset maximum bolus dosage.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 4 and 5 are elevational views illustrating the housing of a bolus device according to some embodiments of the present invention;

FIGS. 6 and 6A are sectioned views showing a bolus device, according to embodiments of the present invention, ready to be activated.

FIG. 9 is sectioned elevational view of the spring assembly;

FIGS. 10A, 10B is isometric enlargement view of the locking mechanism of the selected dose volume;

FIG. 11 is an isometric view showing the reservoir and adjustment ring and locking pin;

FIG. 12 is an isometric view showing the plunger and adjustment ring and locking pin;

FIG. 13 is an expanded isometric view of a part that controls the device volume; the adjustment ring and locking pin;

FIG. 21 is a flowchart of a method according to embodiments of the present invention.

Figure 1:
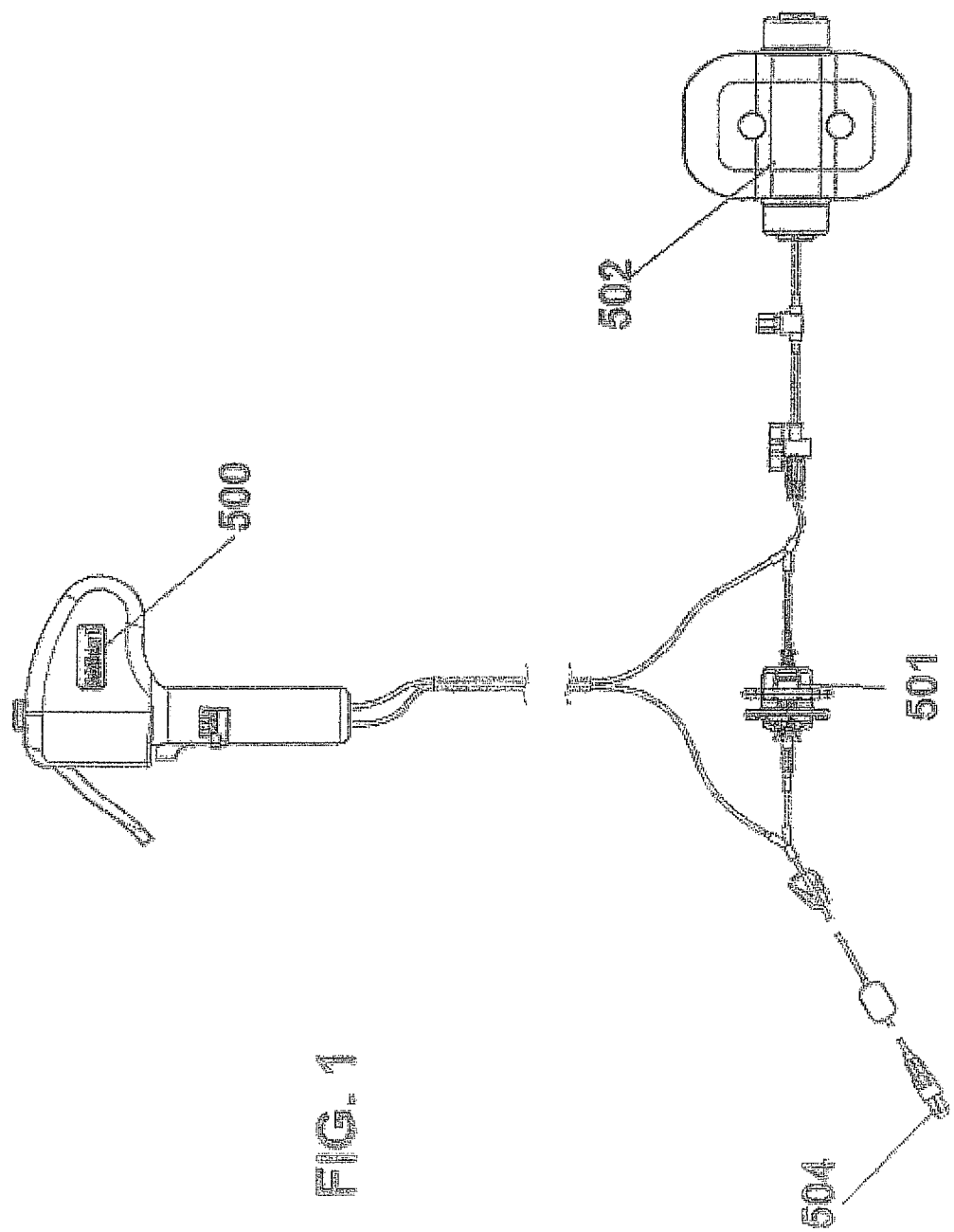
FIG. 1 is a diagrammatic view of a system for self-administration of treatment fluids, connected in parallel according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. It would be further understood by those skilled in the art that the use of absolute directions (e.g., up, down, low, high etc.) and reference points (e.g., lowest, highest, etc.) for describing modes of operation, is for the sake of clarity and that all the directions and reference points in the application are relative and depends on the orientation of the system and device.

Figure 3:
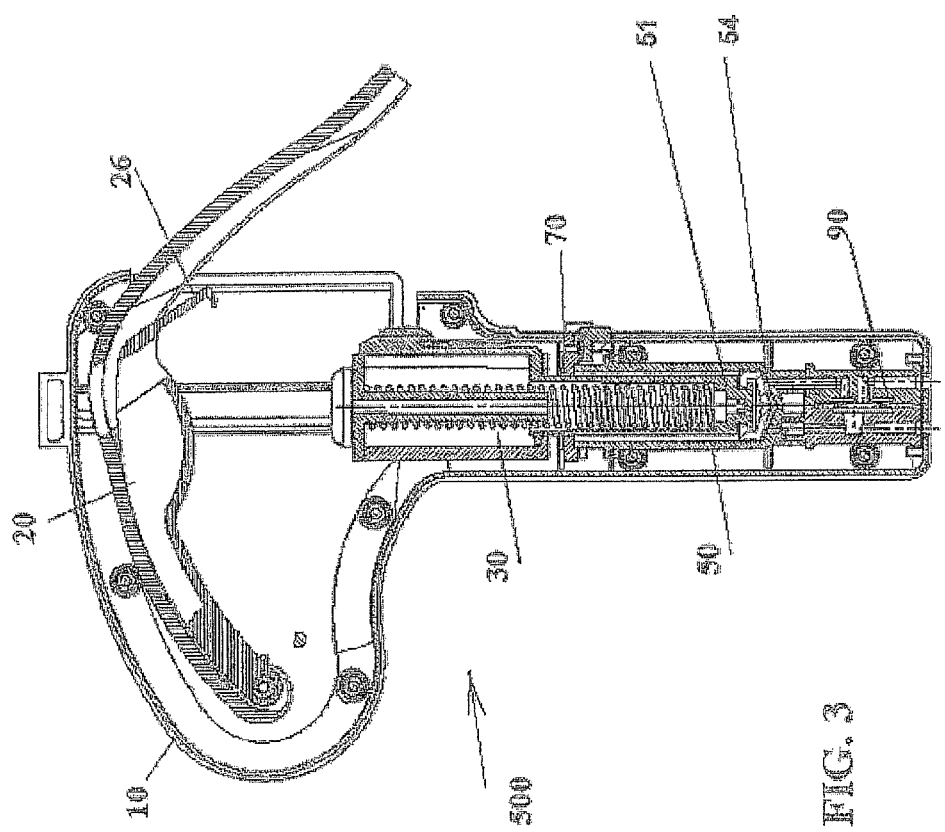
FIG. 3 is a sectioned elevational view of a device according to embodiments of the present invention, showing the plunger at the bottom of its stroke, the position just before the device began to re-fill or fill the initial filling.

A bolus self-administration device 500 is conceptually described in FIG. 3. Device 500 may have six main sections, seen without detail in FIG. 3: a housing 10; levers and associated parts 20; a compression spring, a spring cage and associated parts 30; a reservoir and plunger 50; a dose adjustment mechanism and lock 70; an inlet and outlet ports, valve and capillary restrictor 90.

FIG. 1 shows the bolus device 500 connected in parallel to a prior-art flow controller 501. Both said components connect to an elastomeric reservoir 502 at their inlet ports and to standard male lure connector 504 to be connected to catheter (not shown), that is to be inserted into the patient.

Figure 2:
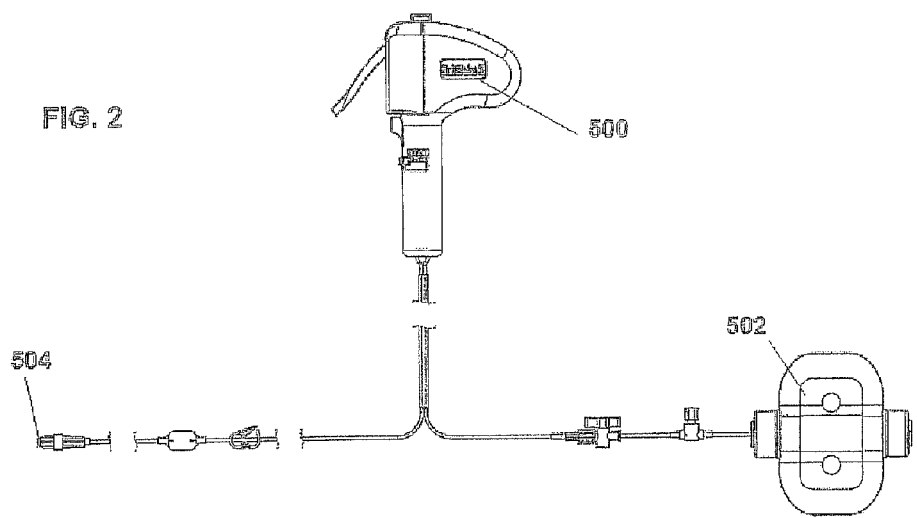
FIG. 2 is a diagrammatic view of a system for self-administration of treatment fluids, connected in series, according to another embodiment of the present invention.

FIG. 2 shows the bolus device 500 connected in series between the exit port 504 and the elastomeric reservoir 502.

FIG. 3 shows the main components of the bolus unit, as listed previously. The plunger 51 is seen in FIG. 3 is in a position reached after having expelled the fluid from the reservoir 54 (or prior being connected the first time to elastomeric reservoir 502).

In FIGS. 4 and 5, there is seen the bolus unit housing 10 which comprises a left shell 11 and a right shell 12. The shells 11, 12 are connected together to form a housing 10 which is part of a disposable bolus device 500. After manufacture, shells 11,12 are connected, for example, by guiding pins and suitable holes. Edge design enables to align and connect shells 11,12 to each other during assembling. Bounding material (e.g., glue, solvent) serves to permanently connect shells 11,12 to create housing 10.

Figure 8:
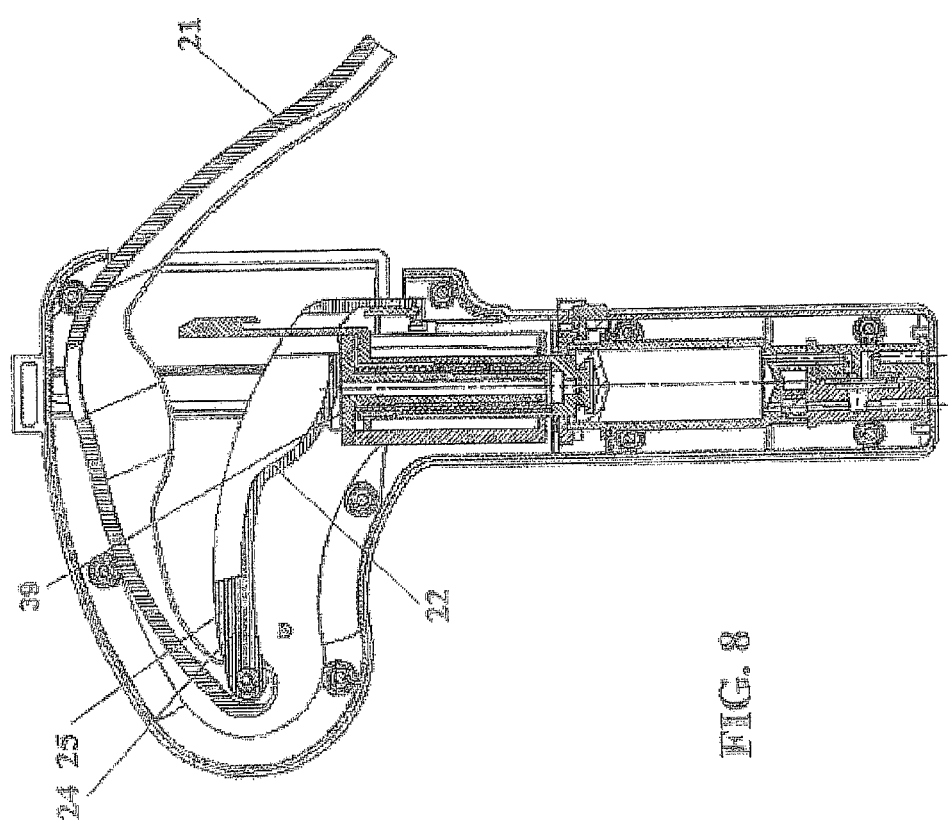
FIG. 8 is a sectioned elevational view of a bolus device according to embodiments of the present invention, showing the plunger at the start of its stroke after the device has been activated and in its' automatic active phase.

The lever assembly 20 is best seen in FIGS. 3, 6 and 6A. External lever 21 is positioned over internal lever 22 and both levers are pivoted by pin 23. Torque springs 24 and 25 each urges one of the levers 21, 22 to an elevated position. In FIG. 8, the internal lever 22 is temporarily retained in its lowest position by a lock tooth 26 over projection 101. The lever 22 applies a compressive force to the cap 39 (FIG. 9) which presses down the spring cage 36 to fully compress the spring 31. Spring 31 applies force over piston 52 to create sufficient pressure in the medication in reservoir 54.

In FIG. 6, both levers 21, 22 and the plunger 51 are seen in their upper positions; medication been filled to the maximum volume, the device is ready to be activated. In the figure, one can see the piston and plunger and reservoir assemblies 50. Plunger 51 with piston 52 are positioned inside the circular cylinder bore 53 of the reservoir 54. The internal surface of the bore 53 is lubricated preferably by a medical grade lubricant to reduce friction and thus to facilitate linear movement between plunger 51 with its attached piston 52 along reservoir 54.

The starting upper position of the plunger 51 relative to the reservoir 54 is adjustable so that the bolus unit can be set to deliver less than a maximum dose volume. The incoming solution gradually fills the reservoir 54 from inlet port 91 through capillary tube 92 and lifts the plunger 51 to an upper position. The piston 52 is provided with a circular undercut 56 that is positioned over a peripheral projection 57 of the plunger 51, seen most clearly in FIG. 9. The reservoir 54 is positioned to and held by the housing 10 at a desired height by means of a peripheral external groove 55.

Figure 7:
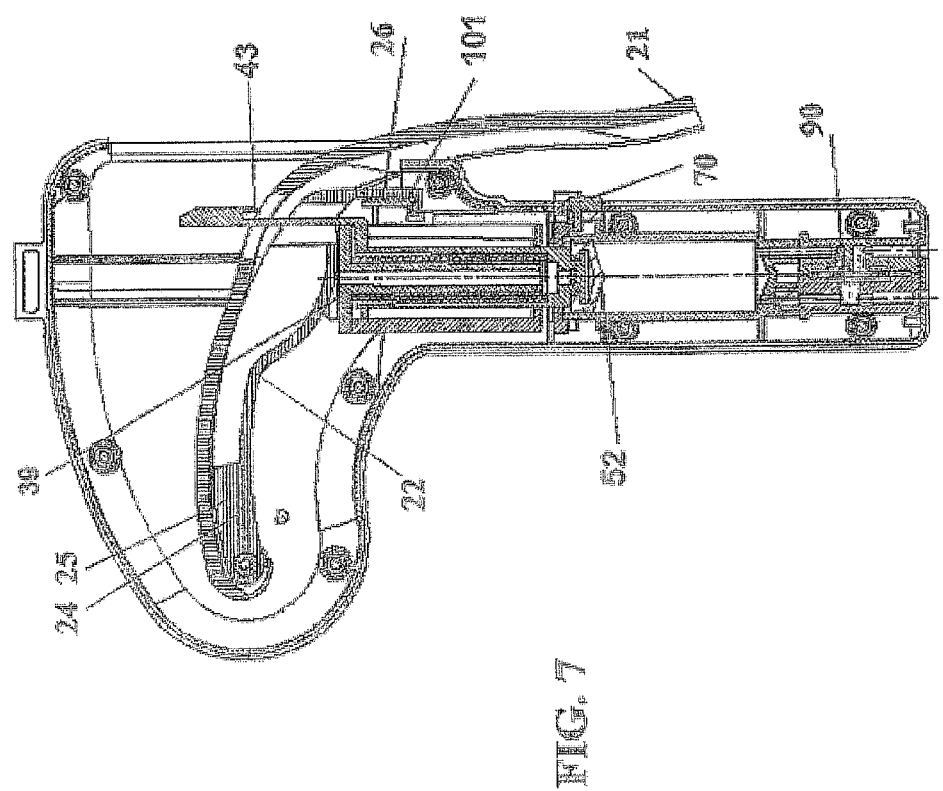
FIG. 7 is a sectioned elevational view showing the external lever of a boluse device according to some embodiments, having been pressed to activate the bolus device.

FIG. 7 shows the internal lever 22 being forced into its lowest position by the external lever 21, which has been pressed to its lowest position by a patient so as to activate the bolus flow. When inner lever 22 is forced all the way down, lock tooth 26 catches projection 101, thus, when external lever 21 is released, spring 24 urges it to its upward position while inner lever 22 remains in its downward position (as shown in FIG. 8).

Turning now to FIG. 9, there is seen the spring assembly 30. A heavy-duty coil compression spring 31 is seen in its preloaded configuration, meaning that the spring is partly but not fully compressed. The lower portion of the spring 31 is positioned inside the cylindrical bore 33 of the plunger 51. The upper portion of the spring is seen in the spring cage 36.

Cap 39 may be permanently attached to spring cage 36 by typically guiding pins and suitable holes that are bonded together using glue during manufacturing. A cylindrical projection 32 being connected to the bottom of cap 39 locates the spring 31 on the central axis of the spring cage 36.

The spring cage 36 comprises a wall 37 seen on the left side of the drawing and an extension rod 38 on the opposite side which is part of the plunger 51.

Figure 8A:
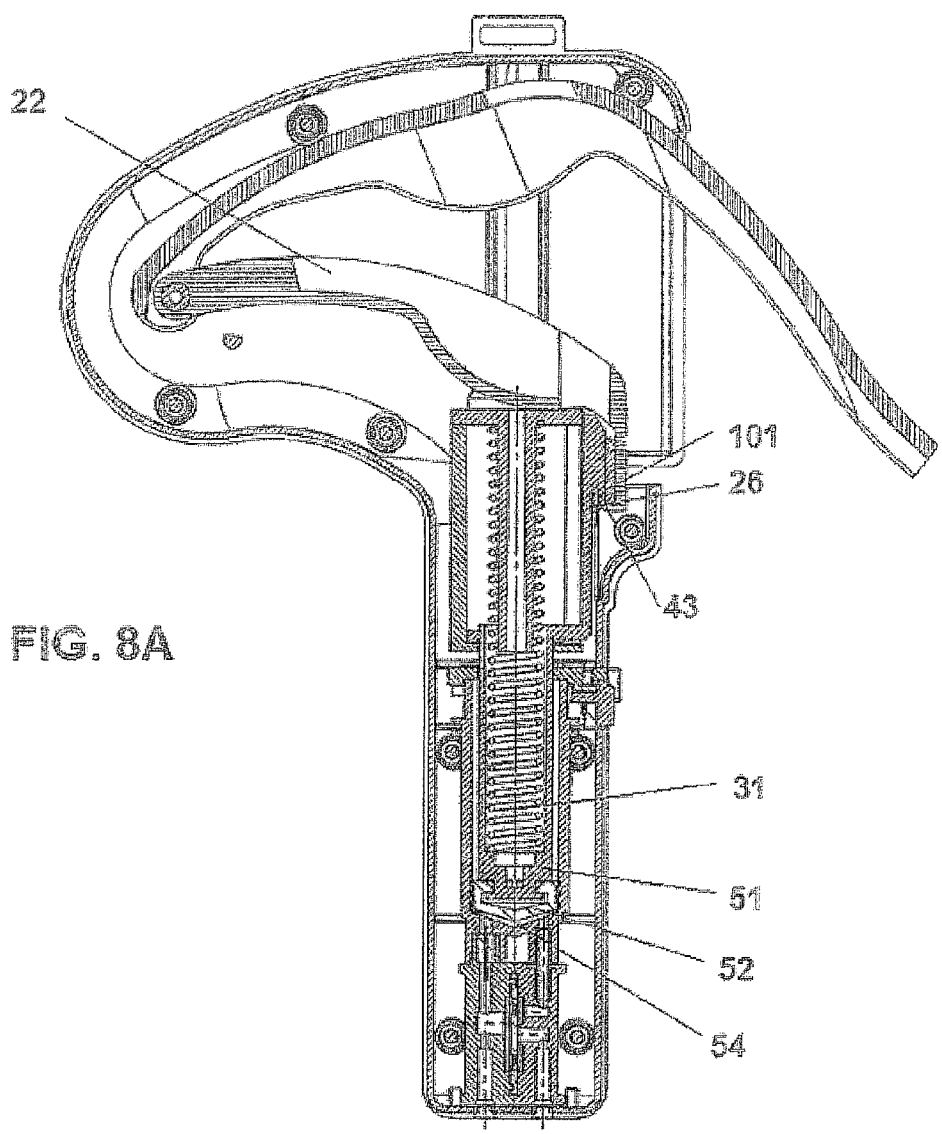
FIG. 8A is a sectioned elevational view showing bolus device just when the reservoir is almost empty and just prior the inner lever is released.

The compression spring 31 axially pushes down the plunger 51, to expel the fluid from the reservoir 54, seen in FIG. 8A.

Full compression of the spring 31 is seen in FIG. 6.

Ring-like side projection 53 of plunger 51 serves as the lower stopper of plunger 51 inside spring cage 36.

An aperture 41 at the base of the spring cage 36 allows the plunger 51 to enter the spring cage 36, as illustrated in FIG. 9.

Figure 10:
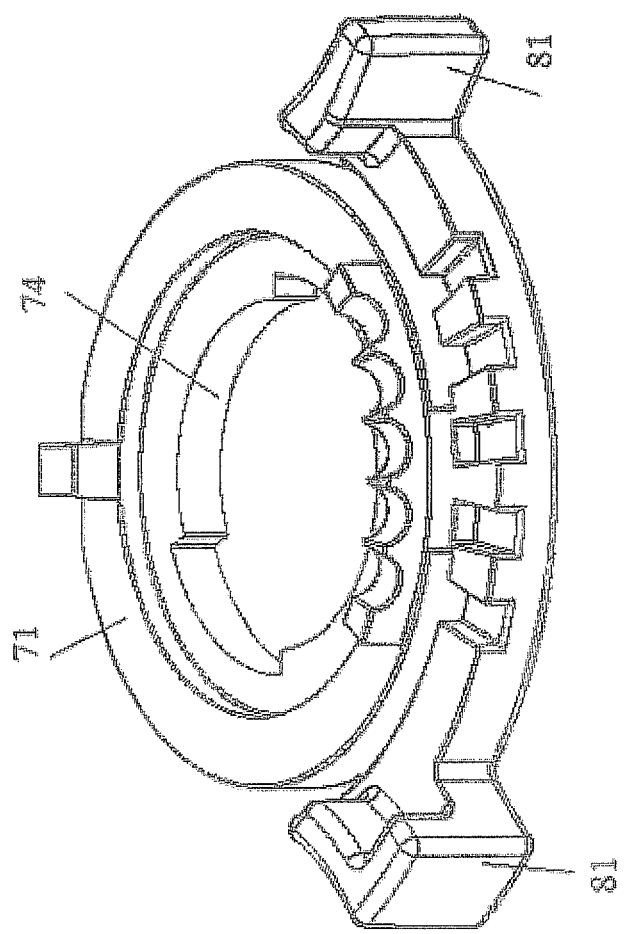
FIG. 10 is an isometric vertically-reversed view of the adjustment ring.

The dose volume adjustment mechanism and lock 70 is seen in FIG. 10 without the locking pin 83 and in FIGS. 10A, 10B, 11, 12, 13 and 14 with the locking pin 83.

The adjusting ring 71 is shown upside down for illustrative purposes in FIG. 10. The internal bore 74 of the ring 71 allows axial movement there through of the plunger 51. Rotational movement of the adjusting ring 71 is restricted by end of openings 111, 112 of shell 11 and shell 12, as seen in FIGS. 4, 5, and bridge section 77, as seen in FIG. 10

The ring 71 is connected to a rotationally sliding handle 75 trough bridge section 77 provided with a plurality of notches 76. Turning the adjusting ring 71 is performed by moving handles 81. Round projections 701 in both handles 81 are engaged in plural dents 114 in shells 11, 12 (FIGS. 4, 5) to position ring 71 at the rotational position of the selected dose volume.

The rotationally sliding handle 75 is seen again in FIG. 11, and erects through opening 111, 112 (see FIGS. 4, 5) in the housing 10. When contacting one of the external steps 78 (see FIG. 12) of the plunger 51, the side walls of bore 74 acts as a stop to the upward movement of the plunger, thereby limiting the volume of fluid allowed into the reservoir 54. Dents 80 in bore 74 allow free pass to the un-active steps 78.

Seen in FIG. 10A, head 84 of lock pin 83 is positioned horizontally. The body 85 of the lock pin has a semi-circular profile and, positioned out of the semicircular profiles 86, does allow position ring 71 rotational movement. Body 85 is positioned in housing 10 with slight preload (between shell 11 to shell 12). Said preload creates sufficient friction to eliminate free movement at any direction of lock-pin 83 (circular and linear). Head 84 is positioned out of dent 120 of housing 10.

Seen in FIG. 10B, head 84 of lock pin 83 is positioned vertically. The body 85 of the lock pin has a semi-circular profile and positioned in one of the semicircular profiles 86; thus, position ring 71 is secured and can't move rotation wise. Projection 88 eliminates lock-pin 83 of sliding out from body 10. Having head 84, being turned back to horizontally position, will again allow rotational movements of position ring 71 to re-set the device active dose volume.

Seen in FIG. 13, the position ring 71 is permanently locked in the selected dose volume. Head of lock pin 83 is vertically positioned, the semi-circular profile of body 85 of lock-pin 83 sits in one of the semicircular profiles 86, head 84 of lock-pin 83 is linearly positioned in dent 120 of housing 10, and projection 87 of lock-pin 83 in engaged in one of dents 76 of position ring 71 to provide additional secured locking.

Figure 14:
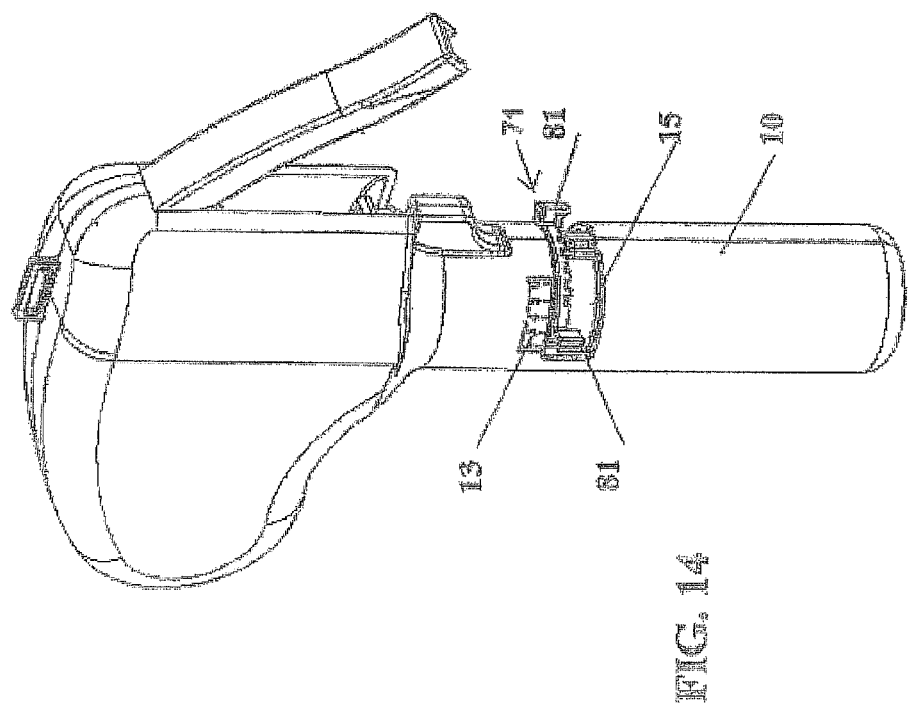
FIG. 14 is an isometric view of the bolus device illustrating how the device active volume may be set.

FIG. 14 illustrates how the user may set adjusting ring 71 to select the required active dose volume; simply dial ring 71 by both handles 81 to align the edge of handle 81 with one of the lines in scale 13. The scales appear on the housing 10. A housing circular dent 15 is provided to allow the circular movement of handles 81

Figure 15:
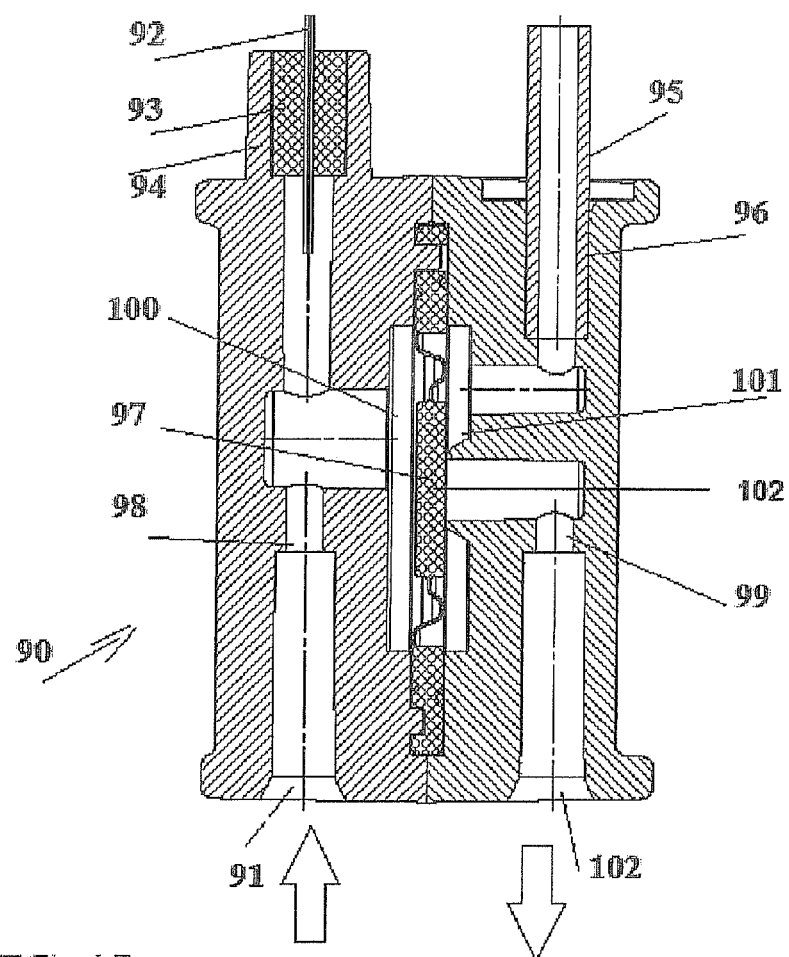
FIG. 15 is a sectioned elevational view of the lower portion of the booster showing the hydraulic valve and inlet/outlet ports and capillary restrictor.
Figure 19:
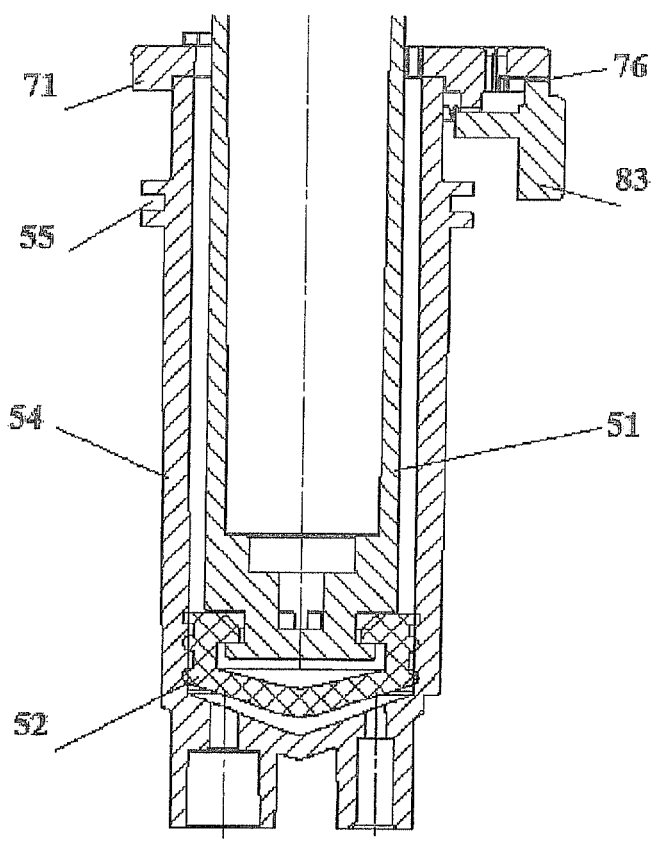
FIG. 19 is a sectioned elevational view of the upper portion of the embodiment seen in FIG. 15.

The in-out ports and valve 90 are seen in FIG. 15. The upper portion needed to complete the bolus device is seen in FIG. 19.

As seen in FIG. 15, the bolus device inlet port 91 leads to a capillary tube 92, which is positioned and fixed inside elastomeric rod 93. Rod 93 may retain capillary tube 92 in place and acts as a sealant to prevent flow of pressurized fluid not through capillary tube 92. Thus, it can be ensured that the entire volume of solution that enters through inlet port 91 flows through capillary tube 92, which acts as a flow resistor.

An outlet tube 95 is held in an opening 96.

A flexible diaphragm 97 is exposed to both inlet 98 and outlet 99 passages. The exposure area 100 of the inlet passage 98 is however much larger than the exposure area 101 of the outlet passage 99 leading to the outlet 102.

IN OPERATION, the pressured solution is introduced to inlet port 91. The solution flows through the capillary tube 92. Pressure (from the left side as seen in the drawing of FIG. 15) of the incoming solution is applied on the diaphragm 97, in response to which the center section of the diaphragm 97 seals opening 101. This eliminates any flow toward exit port 102.

The capillary tube 92 serves as a flow restrictor that determines the bolus device lockout time; that is, the minimum time needed for the reservoir 54 to refill. The solution continues to flow from the capillary tube 92 into the reservoir 54. The limited space between piston 52 and the bottom of the reservoir 54 is filled by the pressurized solution. Since the surface of the diaphragm 97 facing circular area 101 is smaller than the surface of said diaphragm facing circular space 100, exit opening 102 is sealed, and there will be no flow through the passage 99. As solution pressure rises, the piston 52 with plunger 51 is driven vertically upward together with the compressing spring 31. When one of the plunger external steps 78 impacts the ring 71, the vertical upward movement of plunger 51 will be stopped. Meanwhile, the reservoir 54 been filled up to the selected dose volume.

To activate the bolus device, the user presses external lever 21 all the way down until the down movement of internal lever 22 is restricted. Internal lever 22 is positioned under lever 21. Therefore, pressing down lever 21 will also press down lever 22, and lever 22 will press down cap 39 and therefore load the coil spring 31. Once pressed all the way down, the locking tooth 26 of the internal lever 22 engaged over projection 101 seen in FIG. 7. The torque spring 25 returns lever 21 to its up position, once it is released by the user. Internal lever 22, however, remains temporarily locked, as seen in FIG. 8. The loaded coil spring 31 applies force to plunger 51 and so to piston 52 that creates high pressure in the solution locked in the reservoir 54. Due to its high resistance to flow, capillary tube 92 serves substantially as a one-way valve that eliminates any significant back flow toward inlet port 91. The higher fluid pressure on the outlet side at area 101 now pushes the diaphragm 97 towards the left as seen in the drawing of FIG. 15. Thus, opening 102 is not sealed anymore; the fluid flows through tube 95, area 101, passage 99 and out of the outlet port 102. As the plunger 51 with piston 52 reach their bottom position (FIG. 8A), the fluid pressure at circular area 101 is reduced, causing the central section of the diaphragm 97 to be pressed to the right and seal opening 102.

Rerelease tooth 43 of plunger 51 releases the locking tooth 26 of internal lever 22 from of projection 101 (as seen in FIG. 8A).

Spring 24 urge Inner lever 22 to return to its upper position (seen in FIG. 3). Spring 31 is released, and reservoir 54 starts to be refilled through capillary tube 92.

The plunger 51 is lifted by fluid under pressure entering the reservoir 54.

The bolus device lockout time is controlled by the length and inner diameter of the capillary tube 92, i.e., so that too frequent of delivery of additional analgesic, which may harm the patient, is prevented. However, the patient may reactivate the external lever 21 while the internal lever 22 is still at its down position.

Such action has no effect on the refilling of the reservoir 54, yet may provide a placebo effect of benefit for the patient.

Figure 16:
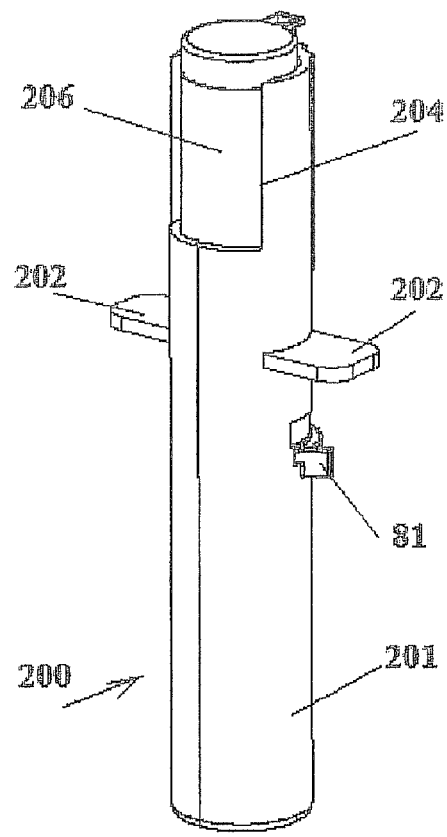
FIG. 16 is an isometric elevational view of a syringe-like bolus device.
Figure 17:
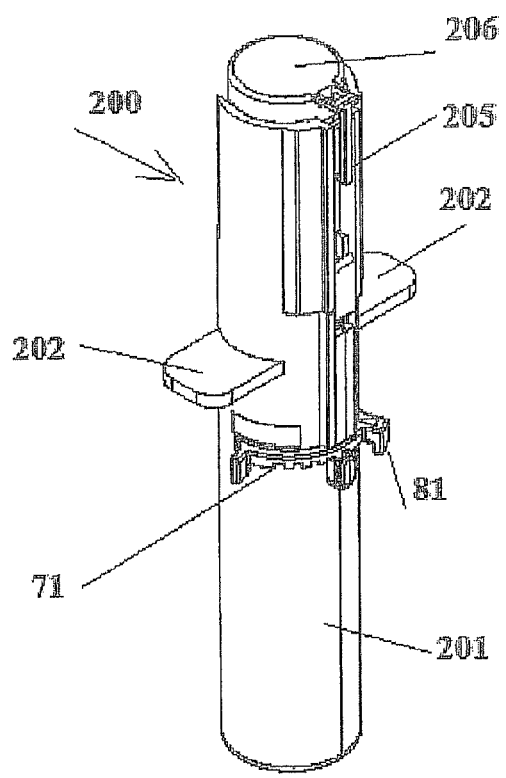
FIG. 17 is an isometric elevational of the syringe-like bolus device showing some detail of retainer catch and how the device active volume may be set.
Figure 18:
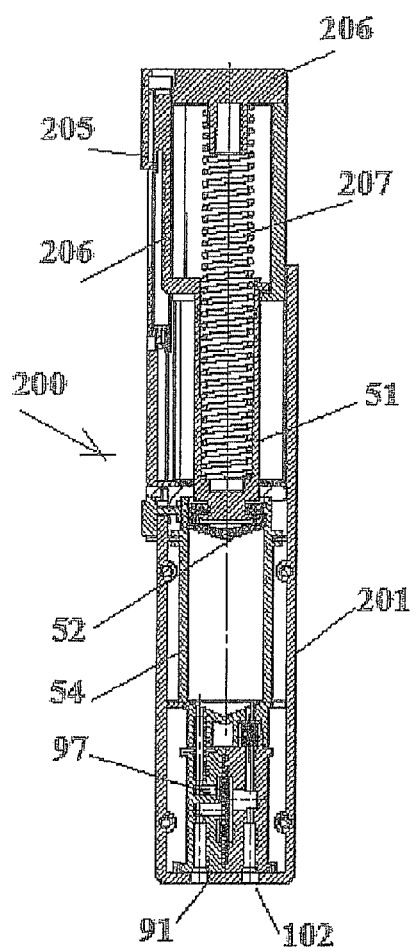
FIG. 18 is a sectioned elevational view of the syringe-like bolus device.

Seen in FIGS. 16, 17 and 18 is a second embodiment of the invention wherein the bolus device 200 is operated by hand in a manner similar to the operation of a standard syringe. The hand levers seen in the previous embodiment have been eliminated and the booster housing 201 is much more compact. Finger grips 202 for retaining the bolus device during actuation are seen projecting from the housing 201. Clearance 204 is provided for the thumb of the user when pressing down the spring cage 206. The coil spring 203 is arranged to require less force for compression so that thumb pressure on the plunger head 204 is sufficient for activation.

The bolus device 200 is intended primarily for the infusion of an analgesic having a low viscosity and/or a lower bolus flow rate and/or with catheters of relatively large internal diameter, thus being operated by a lighter spring 207 as compared to the high force spring seen in the previous embodiment to achieve a desired flow rate.

In other respects, the bolus device 200 has the same adjustment and safety features as described with reference to the previous embodiment.

FIG. 19 illustrates the "reservoir and the plunger assembly" (section 50 FIG. 3). This section of the bolus device is coaxially connected and sealed together with the "valve assembly" presented in FIG. 15.

Figure 20:
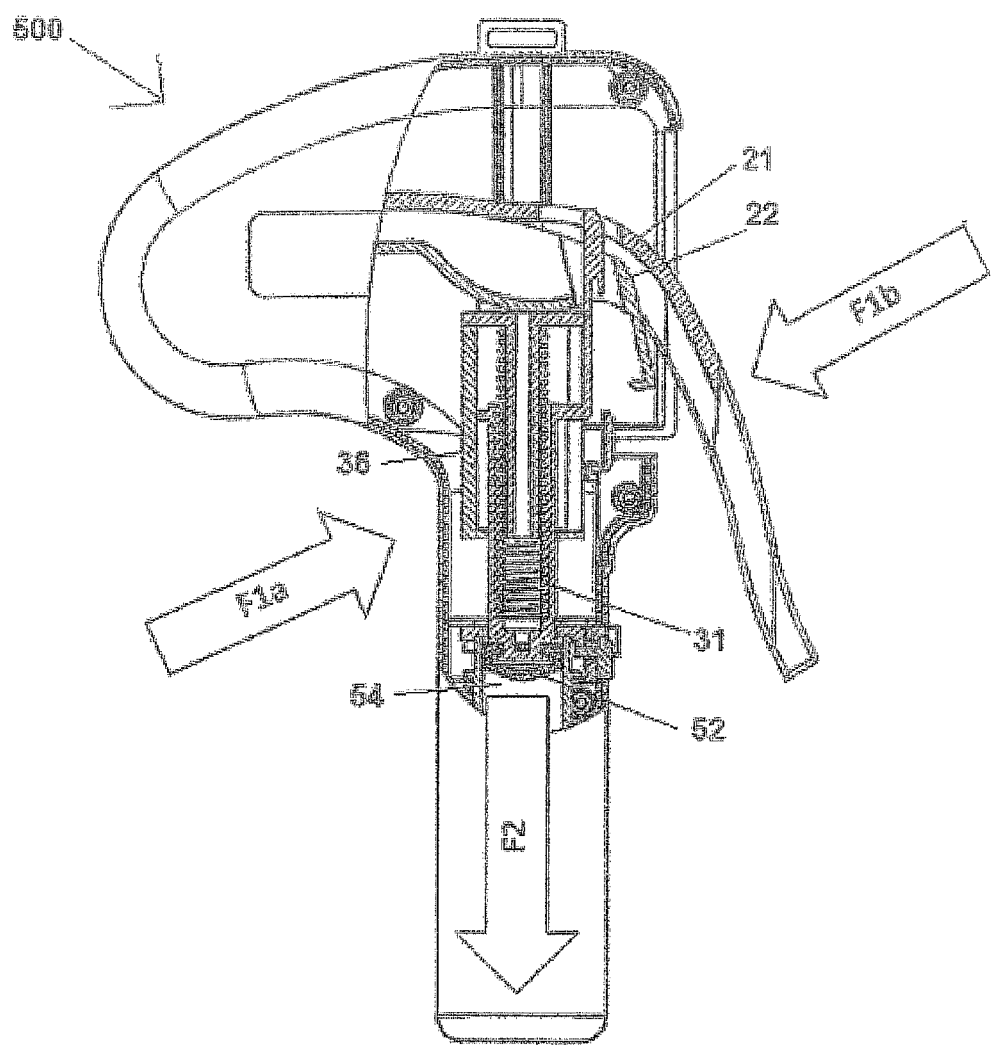
FIG. 20 is a schematic illustration of the forces applied during operation of the bolus self-administration device according to embodiments of the present invention.

As may be seen in FIG. 20, the design of self-administration device 500 allows the conversion of two substantially equal opposite forces F1a and F1b applied by a user or patient, to a third force F2, applied through levers 21 and 22 over compresses spring cage 36 and therefore to fully compress spring 31. Spring 31 in turn applies force over piston 52 to create pressure in internal reservoir 54 and as a result to release treatment fluid from reservoir 54 through outlet 102 (not seen in FIG. 20). It would be appreciated by those skilled in the art that the conversion of two forces F1a, F1b into a single force F2 allows to create sufficient pressure of fluid in reservoir 54 to release the fluid at flow rate of 5 ml/min to 10 ml/min through narrow catheter diameter such as 21 G, as force F2 substantially equals the sum of the absolute values of F1a and F1b.

FIG. 21 illustrates a method for self-administration of a bolus dosage of treatment fluid, the method comprising the following steps:

Actuating an external lever projecting from a patient controlled device for self-administration of treatment fluids to a patient body [block 2010].

Pushing, by external lever, an internal lever mutually pivoted therewith by a pin [block 2020].

Fully compressing a partially loaded compression spring [block 2030].

Temporarily locking internal lever in an inactive position when said compression spring is fully compressed [block 2040].

Pressurizing treatment fluid, contained within an internal reservoir, by said compression spring [block 2050]. The compression spring may apply force to a piston, which in turn may pressurize fluid in internal reservoir.

Releasing substantially all the volume of the treatment fluid in internal reservoir through an outlet of the patient controlled device to a catheter [block 2060].

Releasing temporary locking of internal lever from inactive position to an active position when internal reservoir is empty [block 2070].

It would be appreciated by those skilled in the art that the method may further comprise refilling the internal reservoir with treatment fluid from an external infusion pump.

It would be further appreciated that the maximum bolus dosage releasable in each activation of said patient controlled device may be controlled and preset by a user or a medical staff member, and may be locked from further changing dosage to prevent administration of doses different from said preset dosage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A patient controlled device, for self-administration of medication, comprising:
   a housing;
   a first lever projecting from said housing;
   a spring cage axially movable relative to the housing;
   a compression spring contained at least partially within said spring cage;
   a plunger axially movable relative to the spring cage and the housing;
   a second lever, internal to said housing, wherein said first lever and said second lever are pivoted by a mutual pin, and wherein said second lever is adapted to apply force to the spring cage to move the spring cage toward the plunger and compress the compression spring;
   an internal reservoir;
   a fluid inlet; and
   a fluid outlet;
   wherein said compression spring is adapted to apply force to said plunger when compressed by said spring cage to release a medication bolus dosage from said internal reservoir through said fluid outlet.

2. The device of claim 1 further comprising a dose adjustment mechanism adapted to set the volume of fluid allowed into said internal reservoir.

3. The device of claim 1 further comprising a lock tooth adapted to temporarily retain said second lever in an inactive position until said internal reservoir is empty.

4. The device of claim 3 wherein said plunger further comprises a release tooth, said release tooth adapted to release said lock tooth when said internal reservoir is empty.

5. The device according to claim 4 further comprising a lever spring to return said second lever to an active position when said lock tooth is released.

6. The device of claim 1 further comprising a diaphragm adapted to prevent flow through said fluid outlet when said second lever is in an active position and to prevent back flow from said internal reservoir through said fluid inlet when fluid is released from said internal reservoir.

7. The device of claim 1, further comprising a capillary tube adapted to control the flow rate into said reservoir.

8. A patient controlled system for self-administration of a treatment fluid, comprising:
   an external infusion reservoir;
   a patient controlled device, for self-administration of treatment fluid to said patient body, said patient controlled device comprising:
   a housing;
   a spring cage axially movable relative to the housing;
   a compression spring contained at least partially within said spring cage;
   a plunger axially movable relative to the spring cage and the housing;
   a first lever projecting from said housing;
   a second lever, internal to said housing, wherein said first lever and said second lever are pivoted by a mutual pin, and wherein said second lever is adapted to apply force to the spring cage to move the spring cage toward the plunger and compress the compression spring;
   an internal reservoir;
   a fluid inlet; and
   a fluid outlet;
   a hydraulic valve, positioned at said device fluid outlet, for preventing flow when said patient controlled device is inactive; and
   a catheter connected to said fluid outlet of said patient controlled device;
   wherein said compression spring is adapted to apply force to said plunger when compressed, to release a medication bolus dosage from said internal reservoir through said fluid outlet to said catheter.

9. The system of claim 8 further comprising a dose adjustment mechanism adapted to set the volume of fluid allowed into said internal reservoir.

10. The system of claim 8 further comprising a lock tooth adapted to temporarily retain said second lever in an inactive position until said internal reservoir is empty.

11. The system of claim 10 wherein said plunger further comprises a release tooth, said release tooth adapted to release said lock tooth when said internal reservoir is empty.

12. The system according to claim 11 further comprising a lever spring to return said second lever to an active position when said lock tooth is released.

13. The system of claim 8 further comprising a diaphragm adapted to prevent flow through said fluid outlet when said second lever is in an active position and to prevent back flow from said internal reservoir through said fluid inlet when fluid is released from said internal reservoir.

14. The system of claim 8 wherein said patient controlled device is connected to said external reservoir and to said catheter in parallel to allow continues flow of treatment fluid from said external reservoir to said patient body.

15. The system of claim 8 wherein said patient controlled device is connected to said external reservoir and to said catheter in series to prevent continues flow of treatment fluid from said external reservoir to said patient body.

16. The system according to claim 8 wherein said external reservoir is an elastomeric reservoir.

17. The system of claim 8, further comprising a capillary tube adapted to control the flow rate into said reservoir.

18. A method for self-administration of a bolus dosage of treatment fluid by a patient, the method comprising:
actuating a first lever projecting from a housing of a patient controlled device for self-administration of treatment fluids to a patient body, said patient controlled device comprising an internal reservoir, a plunger, a fluid inlet, and a fluid outlet;
pushing, by said first lever, a second lever mutually pivoted therewith to apply force, by the second lever, to a spring cage to move the spring cage toward the plunger and compress a compression spring contained at least partially within the spring cage;
temporarily locking said second lever in an inactive position;
pressurizing treatment fluid, contained within said internal reservoir, by said compression spring;
releasing substantially all the volume of said treatment fluid in said internal reservoir through said fluid outlet of said patient controlled device; and
releasing said temporary locking of said second lever from said inactive position to an active position.

19. The method according to claim 18 further comprising: refilling said internal reservoir with treatment fluid from an external infusion pump.

20. The method according to claim 18 further comprising: presetting a maximum bolus dosage releasable in each activation of said patient controlled device.

21. The method according to claim 20 wherein said preset dosage is lockable, to prevent administration of doses different from said preset dosage.

22. The method according to claim 20 further comprising automatically refilling said internal reservoir with treatment fluid from an external infusion pump, up to said preset maximum bolus dosage.

* * * * *